(12) United States Patent
Becker

(10) Patent No.: US 7,081,136 B1
(45) Date of Patent: Jul. 25, 2006

(54) ADJUSTABLE GEL FILLED MAMMARY PROSTHESIS AND METHOD

(75) Inventor: Hilton Becker, Boca Raton, FL (US)

(73) Assignee: Techno Investments LLC, Boca Raton, FL (US)

( * ) Notice: Subject to any disclaimer, the term of this patent is extended or adjusted under 35 U.S.C. 154(b) by 0 days.

(21) Appl. No.: 11/107,956

(22) Filed: Apr. 18, 2005

(51) Int. Cl.
*A61F 2/12* (2006.01)

(52) U.S. Cl. ........................ 623/8; 623/23.64

(58) Field of Classification Search .............. 623/7, 623/8, 23.64–23.68
See application file for complete search history.

(56) References Cited

U.S. PATENT DOCUMENTS 4,643,733 A * 2/1987 Becker .................... 623/8
4,944,749 A * 7/1990 Becker .................... 623/8
5,507,808 A * 4/1996 Becker .................... 623/8
6,183,514 B1 * 2/2001 Becker .................... 623/8

* cited by examiner

*Primary Examiner*—David J. Isabella
(74) *Attorney, Agent, or Firm*—Lowe Hauptman & Berner, LLP

(57) ABSTRACT

An adjustable gel filled mammary implant includes inner and outer envelopes with the outer envelope containing about 95% of its volume filled with a silicone gel or the like. The inner envelope is attached to a bottom portion of the outer envelope and defines a volume of about 5%–10% of the volume of the outer envelope and is filled with saline. The implant also includes a self-sealing valve, filling tube and mini-reservoir for adjusting the size of the implant. A method for implanting, adjusting the size and removal of the filling tube and mini-reservoir are also disclosed.

23 Claims, 2 Drawing Sheets

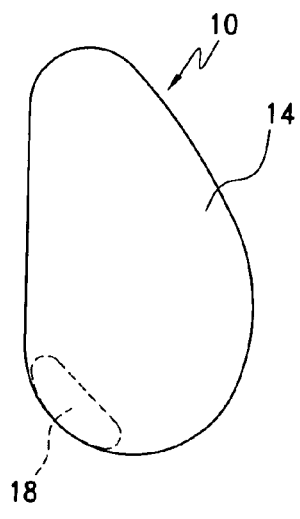
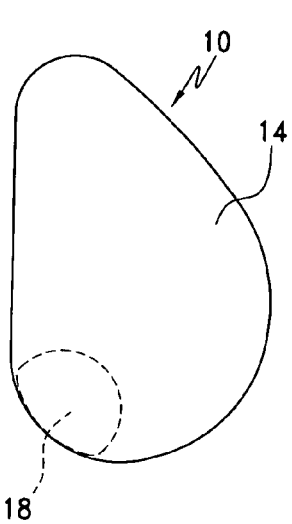
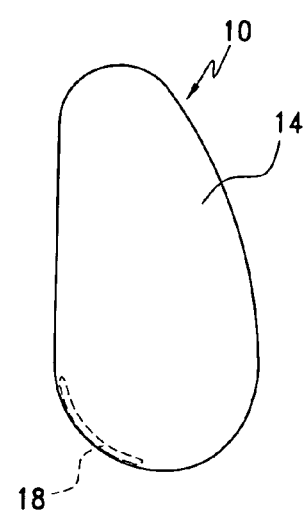
FIG. 5A   FIG. 5B   FIG. 5C
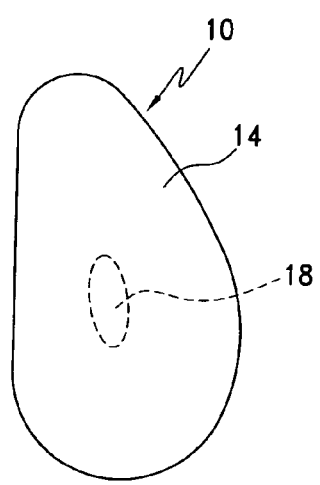
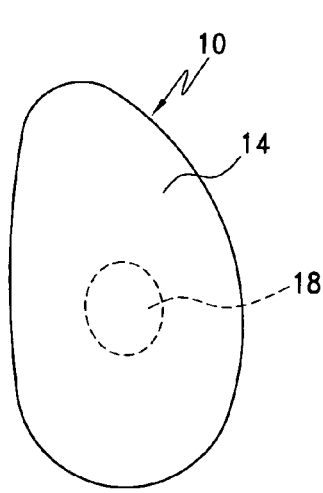
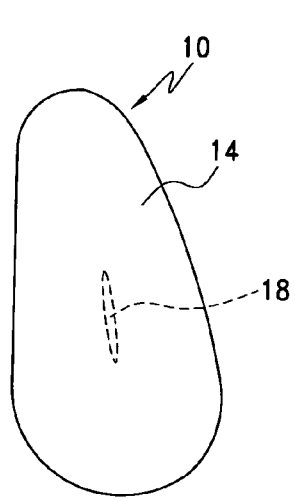
FIG. 6A   FIG. 6B   FIG. 6C

ADJUSTABLE GEL FILLED MAMMARY PROSTHESIS AND METHOD

FIELD OF THE INVENTION

This invention relates to an adjustable gel filled multi-lumen mammary prosthesis for surgical implantation and to a method for implanting an adjustable gel filled multi-lumen mammary prosthesis and for adjusting the size and shape of the prosthesis after a surgical implantation in a patient. More particularly, the invention relates to an adjustable gel filled multi-lumen mammary prosthesis wherein an outer envelope is filled with gel and an inner expandable envelope having a volume o 5–10% compared to the outer envelope. The inner envelope may be left empty or filled to 20–30% of the volume of the outer envelope.

BACKGROUND FOR THE INVENTION

Inflatable implants such as those used in breast reconstruction have been in use for many years. Such implants include at least one and sometimes two soft and pliable members or lumens. The lumens are filled with various materials including saline, silicone gel and the like. For example, one of my earlier U.S. Pat. No. 4,944,749 which issued on Jul. 31, 1990 discloses an implant and inflating construction, which includes inner and outer membranes each having a separate valve. As disclosed therein, the outer membrane contains a viscous gel and the inner membrane is inflated by saline through a removable soft filling tube which passes through the valves.

Concerns over the use of silicone implants led to improved valves as disclosed in my U.S. Pat. No. 5,507,808 for a filling tube and valve construction. As disclosed therein, the valve comprises a short semi-rigid tube that surrounds an opening in a membrane and extends inwardly on the membrane and into the chamber. The semi-rigid tube defines a passageway extending therethrough and also defines a relatively small reservoir which opens into the passageway. A filling tube comprises a soft and flexible length of tubing and a solid portion having an outer diameter which is slightly larger than the inner diameter of the semi-rigid tube and is stretchable longitudinally to reduce its outer diameter to facilitate passage through the semi-rigid tube. As disclosed, the solid portion is adapted to sealingly engage the semi-rigid tube upon relaxation thereof.

The availability of improved valves and reduced concern about the use of silicone gel have led to an increased interest in silicone filled implants. For example, an improved breast prosthesis is disclosed in my U.S. Pat. No. 6,183,514 for a self-positioning breast prosthesis. As disclosed therein, a dual lumen gravity oriented implant includes inner and outer closed envelopes of a medical grade elastomer. The outer closed envelope is generally tear shaped and filled with silicone gel. The inner envelope which is filled with a saline solution is disposed in a lower portion of the prosthesis and returns the prosthesis to its predetermined orientation when an individual to whom the prosthesis is implanted is in a standing or sitting position.

The disclosures in my above-identified patents are incorporated herein in their entirety by reference.

It is now believed that there may be a significant market for an improved breast prosthesis in accordance with the present invention. It is believed that there should be a significant market for such implants, which provide a more natural feel and relatively light weight. The implants in accordance with the present invention are essentially gel or silicone implants and have all of the advantages of such implants. However, such implants provide for miner adjustments in size and on some tissue expansion without detracting from the advantages of a gel filled implant. In addition, the improved prosthesis in accordance with the present invention allows moderate tissue expansion and final size adjustment.

BRIEF SUMMARY OF THE INVENTION

In essence, the present invention contemplates an adjustable gel filled multi-lumen mammary prosthesis with a natural feel and in a preferred embodiment of the invention a natural shape. The prosthesis in accordance with the present invention includes a gel of a given density such as a silicone or hydrogel and an outer closed envelope of medical grade elastomer. The outer closed envelope which defines the outer shape of the prosthesis is adapted to receive a predetermined volume of the gel and is filled with about 90 to about 95% of its predetermined volume with the gel.

The prosthesis in accordance with the present invention also includes a second chamber i.e., a collapsible and expandable inner closed envelope that can be filled or overfilled with a fluid such as saline. In some cases, the inner chamber may be left empty while in other cases it may be filled, partially filled and subsequently removal of the saline to leave an implant that is solely filled with gel. In other cases only part of the saline may be removed. The collapsible inner closed envelope is sized to receive a predetermined volume of the second fluid to expand the collapsible inner closed envelope to between about 5 and up to about 10% of the volume of the outer closed envelope.

A self-sealing valve is disposed in at least one of the envelopes and at times in both envelopes. In addition, a removable soft and flexible filling tube having first and second ends passes through the valve and into the inner envelope. A mini-reservoir is attached to the filling tube on the outside of the envelopes for percutaneously injecting and/or removing saline from the inner envelope. Then, after adjusting the size of the prosthesis, the filling tube and mini-reservoir are removed through a small incision. Means such as a notch may be provided in a wall of the filling tube or the filling tube is merely cut adjacent to the wall of the membrane.

The invention also contemplates a method for implanting an adjustable gel filled multi-lumen mammary prosthesis and for adjusting the size of the prosthesis after implantation. The method includes the step of providing a gel of a given density and an outer closed envelope of a medical grade elastomer with a predetermined volume and filling the outer closed envelope with a gel to about 90% and preferably to about 95% of its predetermined volume.

In this embodiment of the invention, the method includes the step of providing a second fluid of a given density that is greater than the density of the gel, as for example, saline and a collapsible inner closed envelope of medical grade elastomer with a second predetermined volume. The collapsible inner closed envelope is disposed within the outer closed envelope and is sized to the volume, which is equal to about 5% to about 10% and preferably closer to 5% of the volume of the outer closed envelope. The inner closed envelope is optimally filled to about 5 or 10% of the volume of the outer closed envelope and subsequently the size of the implant is adjusted by adding or removing saline percutaneously. The envelope may contain no saline when collapsed, 10% saline when filled or 30% saline when overfilled.

The present invention also contemplates the step of providing a removable soft and flexible filling tube having two ends and a mini-reservoir attached to one end and the other end passing into the inner closed envelope. The self-sealing valve is disposed in the walls of the closed envelopes so that the filling tube passes into the inner envelope. It is also contemplated that two valves may be included in which case the filling tube passes through the valve in the outer closed envelope and through a valve in the inner closed envelope.

The adjustable gel filled mammary prosthesis is implanted into a patient in a conventional manner with a filling tube and mini-reservoir under the patient's skin. And then, saline solution is injected into or removed from the inner closed envelope through the filling tube and mini-reservoir to adjust the prosthesis to a desired size and the mini-reservoir and filling tube are removed from the patient. The filling tube and mini-reservoir can also be use for tissue expansion.

The invention will now be described in connection with the following drawings wherein like numbers have been used to identify like parts.

DESCRIPTION OF THE DRAWINGS

FIG. 5A is a schematic illustration of an implant in accordance with the present invention wherein an inner chamber is fixed to the outer chamber and partially filled with saline;

FIG. 5B is a schematic illustration of the implant shown in FIG. 5A but with the inner chamber with additional saline to change the size and/or shape of the implant;

FIG. 5C is a schematic illustration of the implant shown in FIGS. 5A and 5B but with the saline removed from the inner chamber;

FIG. 6A is a schematic illustration of an implant in accordance with a second embodiment of the invention wherein the inner chamber is free floating after removal of a filling tube (not shown);

FIG. 6B is a schematic illustration of an implant as shown in FIG. 6A but with the inner chamber including additional saline; and, FIG. 6C is a schematic illustration of the implant shown in FIGS. 6A and 6B but with the saline removed from the inner chamber.

DESCRIPTION OF THE PREFERRED EMBODIMENTS OF THE INVENTION

Figure 1:
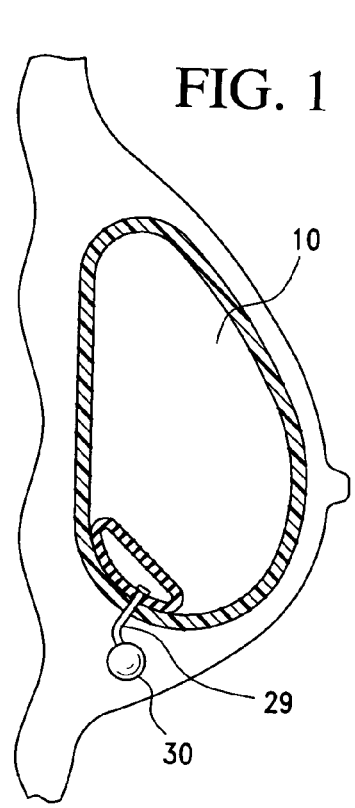
FIG. 1 is a schematic cross-sectional view of a human breast, which has been implanted with a mammary prosthesis in accordance with one embodiment of the invention.

Referring now to the drawings, a mammary prosthesis or breast implant 10 is shown as implanted in the breast tissue 12 of a patient. The implant 10 includes an outer envelope 14 of a medical grade elastomer such as silicone and a silicone gel 16 is contained within the outer envelope 14. The silicone gel 16 may be replaced by other suitable materials such as polyvinyl tyrralidone, hyaluronic acid, polyacrlimides and polysaccharides. In a preferred embodiment of the invention, the silicone gel forms a soft pliable non-fluid mass of material, which approximates the feel of a normal breast as distinguished from the fluid gels used in earlier implants.

The walls of the lumen i.e., the outer envelope 14 and inner envelope 18 may be made of various soft flexible biocompatible materials such as silicone elastomer. Preferred materials include silicone elastomers such as polydimethylsiloxane or polymethylvinylsiloxane or copolymers thereof with other substances. Other polymers may be substituted as will be apparent to those skilled in the art.

In a preferred embodiment of the invention, the outer envelope 14 has an oval or generally tear-shape with a relatively flat rear portion 15 and rounded dome and a forward surface 17. The outer envelope 14 defines an outer lumen which may be of a generally teardrop shape or other nonsymmetrical shape in order to conform to the contours of a human breast. It should be recognize that in certain cases a round shaped may be desired.

The implant 10 also includes an inner lumen which is defined by an inner envelope 18. This inner envelope 18 is preferably made of the same medical grade elastomer as the outer envelope 14. This inner envelope 18 may be of the same general shape as the outer envelope as illustrated in FIG. 1 and is fixed in a lower bottom portion of the outer lumen by conventional means as will be well understood by a person of ordinary skill in the art of designing and manufacturing surgical implants.

The inner lumen or inner envelope 18 also contains a fluid 20 such as a saline solution which has a density which is greater than the density of the gel in the outer lumen. Inner lumen is fixed in a lower bottom portion of the outer lumen so that the center of gravity 18' of the saline filled lumen is sufficiently below the center of gravity of the outer lumen 14' so that the implant will be self-positioning. For example, the inner lumen is substantially contained in the lower bottom portion of the outer lumen so that the denser fluid (the saline solution) will automatically reposition the implant when an individual in whom it is implanted is in a standing, sitting or semi-reclining position.

As illustrated, the outer envelope 14 defines a generally teardrop shape while the inner envelope 18 has a generally crescent shape. Therefore, a mass of the saline filled inner lumen is adjacent to or relatively close to the bottom of the implant 10 while the crescent shape contributes to the overall shape. Having the mass of the saline solution adjacent to the bottom of the implant is believed to optimize the self-positioning feature.

Figure 2:
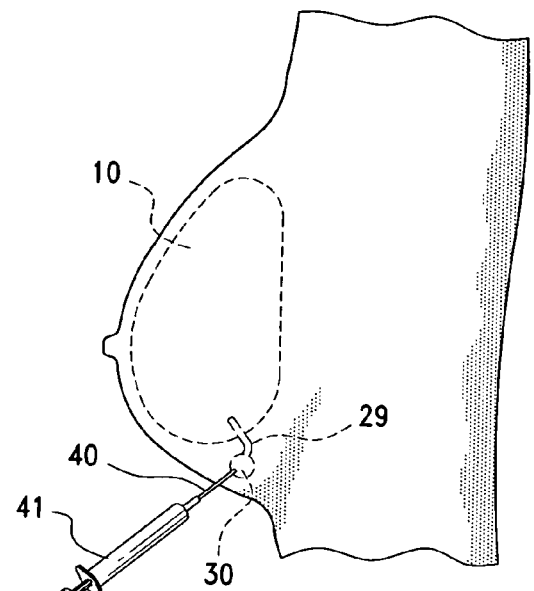
FIG. 2 is an anatomical view showing a percutaneous injection or removal of saline from an inner envelope in accordance with the invention.
Figure 3:
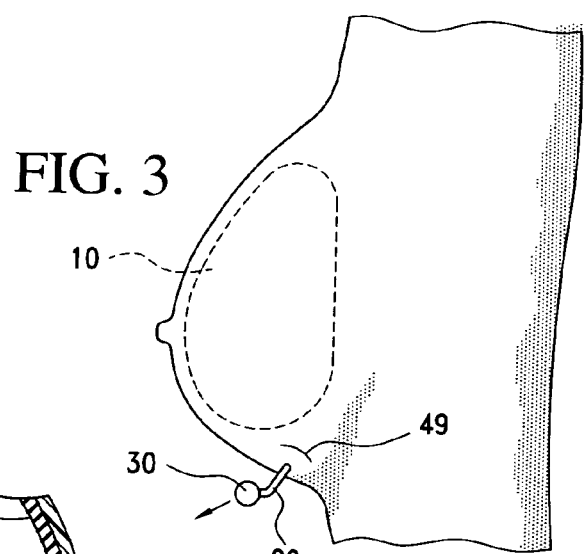
FIG. 3 is an anatomical view showing a mini-reservoir and filling tube detached from an implant and removed from beneath a patient's skin.

As illustrated, in FIGS. 1–3 the breast implant 10 includes a filling tube 29 and mini-reservoir 30 for adding or removing saline 20 to or from the inner envelope 18 of the implant 10. The injection or removal of the saline 20 is made through the mini-reservoir 30 and filling tube 29 and maybe accomplished by means of a needle 40 and syringe 41.

The filling tube 29 and mini-reservoir 30 are preferably placed beneath a patient's skin near the implant and remain in place so long as desired for adjustment in size, as for example four to eight weeks. Then when any desired adjustments have been made, a small incision is made over the reservoir as indicated by 49 in FIG. 3, which is large enough to remove it from beneath the skin. At times, a cut can be made along the original incision line. The mini-reservoir 30 and filling tube 29 can then be detached from the implant 10 and removed from the patient's body as will be well understood by surgeons of ordinary skill in the art.

Figure 4:
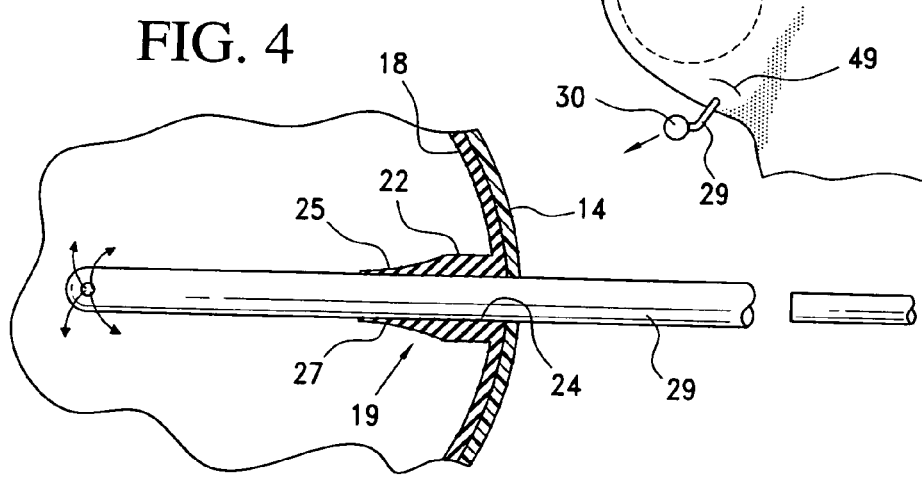
FIG. 4 is an enlarged sectional view of a prior art valve of a type used in one embodiment of the invention.

As shown in FIG. 4, the outer envelope 14 and inner envelope 18 may be fixed together and include a self-sealing valve 19. The valve 19 includes a short connecting tube 22, which surrounds an opening 24 in the envelopes 14 and 18 and extends inwardly thereof. A pair of opposed flaps 25 and 27 extend inwardly of and surround the tube 22.

A filling tube 29 is preferably made of a relatively soft material so as not to puncture the envelopes. The filling tube 29 is shown in an inserted position within the inner lumen and can be inserted at the time of manufacture. Alternatively, a filling tube can be inserted later. In either case, the filling tube 29 extends through the opening 24 and the tube 22 and flaps 25, 27. The distal end of the tube 29 is connected with a source of saline solution not shown and used to add saline to the inner lumen or to remove saline therefrom. Upon completion of the filling and expansion process the filling tube 29 is removed and the self-sealing valve closes. A more detailed description of the self-sealing valve and inflation are disclosed in my previously mentioned U.S. Pat. No. 4,944,749. A further description of an inflatable permanent implant having a detachable filling tube is contained in my earlier U.S. Pat. No. 4,643,733 which is also incorporated herein in its entirety by reference.

As shown in FIGS. 5A–5C a breast implant 10 includes an outer envelope 14 which is filled with silicone gel at an inner envelope 18 which may be filled or partially filled with saline. As shown, the inner envelope 18 is fixed to the outer envelope 14 in a lower portion of the implant. By contrast, FIGS. 6A–6C illustrate an implant 10 wherein the inner envelope 18 is not fixed to a wall of the envelope 14 and is free to float therein after removal of a filling tube (not shown). The use of a filling tube for an inner envelope is well known and well within the ability of a person of ordinary skill in the art.

In essence, the gel filled implant as illustrated contains a second chamber which may be attached to the outer chamber 4 may be free floating as shown in FIGS. 6A–6C. The inner chamber is filled by means of a detachable filling tube and sealed by a contained valve. Further, saline may be added to the inner chamber at the time of surgery or after surgery the saline may be added to a) change the size, b) alter the shape (increase projection) or c) for temporary tissue expansion. It is also contemplated that the inner chamber may be left empty or overfilled to adjust the size or for tissue expansion.

As a result of the above, the implant feels and functions as a gel implant and while it may contain up to 30% saline it will most commonly contain small amounts of saline that would normally be left in the implant. Such amounts would not detract from the implant functioning as a gel filled implant.

While the invention has been described in connection with its preferred embodiments, it should be recognized that changes and modifications may be made therein without departing from the scope of the appended claims.

What is claimed is:

1. An adjustable gel filled multi-lumen mammary prosthesis for surgical implantation comprising:
    an outer closed envelope of medical grade elastomer sized and adapted to receive a predetermined volume of a gel of given density, wherein said outer closed envelope is filled to between about 90–95% of its predetermined volume with said gel;
    a collapsible inner closed envelope of medical grade elastomer disposed within said outer closed envelope, wherein said inner closed envelope is sized to receive a predetermined volume of a second fluid of greater density than the density of said gel in said outer closed envelope, and wherein said collapsible inner closed envelope is filled to between about 5 to about 10% of the volume of said outer closed envelope with said second fluid;
    a self-sealing valve means in said envelopes; and
    a removable soft and flexible filling tube having first and second ends and a reservoir attached to said filling tube at said first end thereof; and wherein said second end of said filling tube passes through said self-sealing valve means and into said inner closed envelope.

2. An adjustable gel filled multi-lumen mammary prosthesis for surgical implantation according to claim 1, in which said gel is a silicone gel.

3. An adjustable gel filled multi-lumen mammary prosthesis for surgical implantation according to claim 1, in which said gel is a hydrogel.

4. An adjustable gel filled multi-lumen mammary prosthesis for surgical implantation comprising:
    an expandable outer closed envelope of medical grade elastomer adapted to receive a predetermined volume of a silicone gel of given density, wherein said outer closed envelope is filled up to about 95% of its predetermined volume with said silicone gel;
    a collapsible inner closed envelope of medical grade elastomer disposed within said outer closed envelope, and wherein said inner closed envelope is sized to receive a predetermined volume of a saline fluid of greater density than the density of said silicone gel in said outer closed envelope to expand said collapsible inner closed envelope to about 5% of the volume of said outer closed envelope;
    a self-sealing valve means; and
    a removable soft and flexible filling tube having first and second ends and a mini-reservoir attached to said filling tube at first end thereof; and wherein said second end of said filling tube extends through said self-sealing valve means and into said inner closed envelope for injecting and removing saline through said mini-reservoir and said filling tube into and out of said inner closed envelope to thereby adjust the size of the implant.

5. An adjustable gel filled multi-lumen mammary prosthesis for surgical implantation according to claim 4, in which said outer closed envelope defines a generally oval or generally tear-shape.

6. An adjustable gel filled multi-lumen mammary prosthesis for surgical implantation according to claim 4, in which said inner closed envelope defines a shape which is generally similar to the shape of said outer closed envelope.

7. An adjustable gel filled multi-lumen mammary prosthesis for surgical implantation according to claim 4, in which said inner closed envelope is fixed to a rear bottom portion of said outer closed envelope.

8. An adjustable gel filled multi-lumen mammary prosthesis for surgical implantation according to claim 4, in which said inner closed envelope is free to move with respect to said outer closed envelope.

9. An adjustable gel filled multi-lumen mammary prosthesis for surgical implantation according to claim 4, in which said valve means comprises a plug valve and a flap valve.

10. An adjustable gel filled multi-lumen mammary prosthesis for surgical implantation according to claim 4, wherein said filling tube and said mini-reservoir are made of a medical grade elastomer.

11. An adjustable gel filled multi-lumen mammary prosthesis for surgical implantation according to claim 4, in which said gel is a soft pliable non-fluid mass of material which approximates the feel of a normal breast.

12. A method for implanting an adjustable gel filled multi-lumen mammary prosthesis and for adjusting the size of the prosthesis after implantation comprising the steps of:
providing a gel of a given density and an outer closed envelope of medical grade elastomer with a predetermined volume and filling the outer closed envelope with a gel to between about 90% to about 95% of the predetermined volume;
providing a saline fluid of a greater density then the density of the gel and a collapsible inner closed envelope of medical grade elastomer disclosed in a bottom lower portion on the outer closed envelope and wherein the inner closed envelope is sized to receive a predetermine volume of the saline solution and filling the inner closed envelope to expand the collapsible inner closed envelope to between about 5% to about 10% of the volume of the outer closed envelope and filling the inner closed envelope with the saline fluid to provide a volume of between about 5% to about 10% of the volume of the outer closed envelope;
providing a removable soft and flexible filling tube having two ends and a mini-reservoir attached to one end and the other end passing through the outer closed envelope and into the inner closed envelope to thereby provide an adjustable gel filled multi-lumen mammary prosthesis having a fill tube and a mini-reservoir attached thereto;
implanting the adjustable gel filled mammary prosthesis in a patient with the filling tube and mini-reservoir under the patient's skin;
percutaneously injecting and/or removing saline solution from the inner closed envelope through the filling tube and the mini-reservoir; and
removing the filling tube and mini-reservoir from the patient.

13. An adjustable gel filled multi-lumen mammary prosthesis for surgical implantation according to claim 1, wherein said second end of said filing tube provides an attachment for a needle or syringe.

14. An adjustable gel filled multi-lumen mammary prosthesis for surgical implantation according to claim 1, wherein said reservoir is adapted to receive a needle or syringe.

15. An adjustable gel filled multi-lumen mammary prosthesis for surgical implantation according to claim 1, in which said outer closed envelope defines a generally oval or generally tear-shape.

16. An adjustable gel filled multi-lumen mammary prosthesis for surgical implantation according to claim 1, in which said inner closed envelope defines a shape which is generally similar to the shape of said outer closed envelope.

17. An adjustable gel filled multi-lumen mammary prosthesis for surgical implantation according to claim 1, in which said inner closed envelope is fixed to a rear bottom portion of said outer closed envelope.

18. An adjustable gel filled multi-lumen mammary prosthesis for surgical implantation according to claim 1, in which said inner closed envelope is free to move with respect to said outer closed envelope.

19. An adjustable gel filled multi-lumen mammary prosthesis for surgical implantation according to claim 1, in which said valve means comprises a plug valve and a flap valve.

20. An adjustable gel filled multi-lumen mammary prosthesis for surgical implantation according to claim 1, wherein said filling tube and said mini-reservoir are made of a medical grade elastomer.

21. An adjustable gel filled multi-lumen mammary prosthesis for surgical implantation according to claim 1, in which said gel is a soft pliable non-fluid mass of material which approximates the feel of a normal breast.

22. An adjustable gel filled multi-lumen mammary prosthesis for surgical implantation according to claim 4, wherein said second end of said filing tube provides an attachment for a needle or syringe.

23. An adjustable gel filled multi-lumen mammary prosthesis for surgical implantation according to claim 4, wherein said reservoir is adapted to receive a needle or syringe.

* * * * *